(12) United States Patent
Viedma

(10) Patent No.: US 7,851,177 B2
(45) Date of Patent: Dec. 14, 2010

(54) METHOD FOR DETECTING PRESENCE OF ACIDOPHILIC MICROORGANISMS IN BIOLEACHING SOLUTION

(75) Inventor: Pabla Viedma, Santiago (CL)

(73) Assignee: Biotechnologias Del Agua Ltda, Santiago (CL)

( * ) Notice: Subject to any disclaimer, the term of this patent is extended or adjusted under 35 U.S.C. 154(b) by 88 days.

(21) Appl. No.: 11/880,565

(22) Filed: Jul. 23, 2007

(65) Prior Publication Data
US 2008/0044841 A1 Feb. 21, 2008

(30) Foreign Application Priority Data
Jul. 31, 2006 (CL) .................................. 2002-2006

(51) Int. Cl.
*C12Q 1/24* (2006.01)
(52) U.S. Cl. .......................................... 435/30; 435/34
(58) Field of Classification Search .................. 435/30, 435/34, 9, 8; 75/743
See application file for complete search history.

(56) References Cited

U.S. PATENT DOCUMENTS

| | | | |
|---|---|---|---|
| 3,971,703 A | 7/1976 | Picciolo et al. | |
| 4,385,113 A * | 5/1983 | Frosch et al. ................... | 435/8 |
| 5,004,684 A | 4/1991 | Simpson et al. | |
| 5,182,202 A | 1/1993 | Kajiyama et al. | |
| 5,258,285 A | 11/1993 | Aegidius | |
| 5,366,867 A | 11/1994 | Kawakami et al. | |
| 5,766,868 A | 6/1998 | Seto | |
| 5,888,725 A | 3/1999 | Sanders | |
| 5,962,247 A | 10/1999 | Foote et al. | |
| 6,653,147 B2 | 11/2003 | DiCesare | |
| 6,660,489 B2 | 12/2003 | Schrecengost et al. | |
| 6,927,851 B2 | 8/2005 | McCaffrey et al. | |
| 7,547,526 B2 * | 6/2009 | Ladisch et al. ................. | 435/30 |
| 2006/0094094 A1* | 5/2006 | Sugio et al. .................. | 435/168 |
| 2008/0102515 A1* | 5/2008 | Morales Cerda et al. .... | 435/262 |

OTHER PUBLICATIONS deBruyn J. et al. Floating Filters, A Novel Technique for Isolation and Enumeration of Fastidious, Acidophilic, Iron Oxidizing, Autotrophic Bacteria. Applied and Environmental Microbiology 56(9)2891-2894, Sep. 1990.*
Tuovinen, Olli; "A Method for the Preparation of Solidified Colloidal Sulphur Media"; Zbl. Bakt. II. Abt. 134, (1979) 108-109.
Harrison, Arthur P., Jr., "The Acidophilic Thiobacilli and Other Acidophilic Bacteria that Share Their Habitat", 1984. Annual Review of Microbiology 38: 265-292.
Johnson, D.B, "Selective Solid Media for Isolating and Enumerating Acidophilic Bacteria", Journal of Microbiol. Methods (1995) 23:205-218.
Lafleur et al, 1993. "Determination of Iron Oxidizing Bacteria Numbers" Biohydrometallurgical Technologies, Ed by A.E. Torma et al., The Minerals, Metals and Materials Society ' pp. 433-441.

Sand et al. "Activity and Occurance of leaching bacteria in mine waste at Cartagena, Spain, in the years 1991 until 2000", 15th International Biohydrometallurgy Symposium, Sep. 14-19, 2003, pp. 997-1002; Athens, Greece.
De Bruyn et al, "Floating Filters, A Novel Technique for Isolation and Enumeration of Fastidious, Acidophlic, Iron-Oxidixing, Autotrophic Bacteria", Applied and Environmental Microbiology, Sep. 1990, pp. 2891-2894.
Escobar et al, "A Method for Evaluating the Production of Free and Attached Bacteria in the Bioleaching of Chalcopyrite with *Thiobacilus ferrooxidanns*"; Hydrometallurgy 40 (1996) 1-10; Received 1996 Aug. 23, 1993; accepted Jan. 3, 1995.
Savic et al, "Contribution to the quantification of the *Acidithiobacillus ferroxidans* biomass concentratration from the oxygen uptake rate"; 15th Intern'l Biohydrometallurgy.
Zanella et al. "Leaching of Sewage Sludge with *Thiobacillus ferrooxidans*: Determination of Physiological Activity via Reduction of a Tetrzolium Salt,"Biohydrometallurgical Technologies, The Minerals. Metals & Materials Society, 1993; pp. 589-593.
Pizarro et al., "Bacterial Populations in Samples of Bioleached Copper Ore as Revealed by Analysis of DNA Obtained before and after Cultivation"; Applied and Environmental Microbiology, American Society for Microbiology, Apr. 1996, pp. 1323-1328.
Espejo and Romero; "Bacterial Community in Copper Sulfide Ores Inoculated and Leached with Solution from a Commercial-Scale Copper Leaching Plant"; Appl. Environ. Microbiol.; Apr. 1997, vol. 63, No. 4, pp. 1344-1348.
Vasquez and Espejo; "Chemolithotropic Bacteria in Copper Ores Leached at High Sulfuric Acid Concetration"; Appl. and Environ. Microbiol.; Jan. 1997; vol. 63, No. 1; pp. 332-334.
Schrenk et al, "Distribution of *Thiobacillus ferrooxidans* and *Leptospirillum ferrooxidans*: Implications for Generation of Acid Mine Drainage"; Science, Mar. 6, 1998; 279; 1519-1522.
Bond et al., "Phylogeny of Microorganisms Polpulating a Thick, Subaerial, Predominatly Lithotropic Biofilm at an Extreme Acid Mine Drainage Site", Applied and Environmental Microbiology, Sep. 2000, vol. 66, No. 9, pp. 3842-3849.
Coram et al, "Molecular Relatinship between Two Groups of the Genus *Leptospirillum* and the Finding that *Leptospirillum ferriphilum* sp. nov. Dominates South African Commercial Biooxidation Tanks That Operate at 40 C", Applied and Environmental Microbiology, Feb. 2002, vol. 68, No. 2, pp. 838-845.
Gonzalez-Toril et al., "Microbial Ecology of an Extreme Acidic Environment, The Tinto River", Applied and Environ. Microbiol., Aug. 2003; vol. 69, No. 8; pp. 4853-4865.
Mitchell et al, "Systematic analysis of our culture colllection for 'genospecles' of *Acidithiobacillus ferrooxidans, Acidithiobacillus thiooxidans* and *Leptospirillum ferrooxidans*", Proceedings of the 15th International Biohydromettallurgy Symposium, Sep. 14-19, 2003; Athens, Greece.
Sala-Newby et al, "Sequesnce and biochemical similarities between the luciferases of the glow-worm *Lampyris noctiluca* and the firefly *Photinus pyralis*", Biochem. J. (1996) 313, 761-767.
Luciferase (LUC-T) from recombinant *E. coli*, kikoman, LUC-T (CD:61315), 199-204.

* cited by examiner

*Primary Examiner*—Ralph Gitomer
(74) *Attorney, Agent, or Firm*—Gottlieb Rackman & Reisman, PC

(57) ABSTRACT

A method of rapid analysis of the presence of active acidophilic microorganisms in a bioleaching solution includes the steps of: concentrating the solution, removing luminescence inhibitory agents from the solution and measuring the luminescence of the solution.

19 Claims, 2 Drawing Sheets

METHOD FOR DETECTING PRESENCE OF ACIDOPHILIC MICROORGANISMS IN BIOLEACHING SOLUTION

FIELD OF THE INVENTION

The present invention is related to the determination of the presence of active acidophilic microorganisms in a water or solid sample, such as those present in bioleaching processes or in acid mine or rock drainages.

OBJECT OF THE INVENTION

The object of the present invention is to provide a rapid, reliable and effective method for detection of the presence of active acidophilic microorganisms in water or solid samples, such as those present in bioleaching processes or in acid mine or rock drainages.

In a further aspect, the invention provides a kit for determination of the viability of acidophilic microorganisms.

DESCRIPTION OF THE PREVIOUS ART

Bioleaching is the dissolution of sulfide ores by using microorganisms. These microorganisms require only very simple inorganic compounds to grow and are often found in hydrometallurgical process waters. A particular feature of these microorganisms is their ability to grow in extremely acid solutions (pH<3), and therefore they are referred to as acidophilic. These microorganisms include different bacteria belonging to genera *Acidithiobacillus, Leptospirillum, Sulfobacillus, Acidiphilium*, etc., some archaea belonging to genera *Ferroplasma, Sulfolobus, Metallosphaera*, etc., and also the presence of some fungi and microalgae has also been detected.

From the last eighties on, the diverse bioleaching processes has been widely disseminated and especially in Chilean copper mining. Accordingly, heap leaching as a complete leaching route, solvent extraction and electrowinning (LX-SX-EW) became one of the most relevant copper mining and metallurgy innovations in the world.

Due to the fact that the entire bioleaching process depends strictly on the presence and viability of microorganisms, it is capital to have methodologies that allow rapid, reliable and effective monitoring of the biological activity in commercial-scale biohydrometallurgical processes. Therefore, during monitoring of sulfide leaching heaps, the existing biological activity must be known at different sampling points in the leaching heap to ensure efficient metal recovery and to take corrective measures whenever necessary (as for instance when inoculating leaching microorganisms, supplying limiting nutrients for biological activity, avoiding the presence of toxic agents, etc.). However, currently there are no modern methodologies that can effectively replace classic techniques for determining total viable bacteria, which have a very long analysis time (between 7 and 14 days) and therefore do not allow carrying out the required corrective actions in time.

Microorganism detection in bioleaching heaps for quality and process control purposes are currently carried out by using different classic methods for determining viable leaching bacteria. These methods are based on determining microbial growth in different adequate culture media. As an example, we can mention the counting method in solid medium developed in 1979 by Tuovinen (Tuovinen, 1979. *Zbl. Bakt. II. Abt.* 134, 108-109). The most efficient counting technique in solid medium currently used was created by Harrison (Harrison, 1984. *Ann. Rev. Microbiol.* 38: 265-292). This method uses two agarose layers with different concentration. This methodology can be considered standard. More recently, Johnson (*J. Microbiol. Methods* (1995) 23:205-18) described a new selective solid medium for isolating and counting acidophilic microorganisms. The Most Probable Number (MPN) statistical technique (Lafleur et al., 1993. "Biohydrometallurgical Technologies", Ed. A. E. Torma, M. L. Apel and C. L. Brierley, The Minerals, Metals and Materials Society, pp. 433-441; and Sand et al. 1993. *Proceedings of the 15th International Biohydrometallurgy Symposium*, Athens, Greece, Sep. 14-19, 2003) has also been used. This technique uses liquid medium culture. However, these media only allow partial recovery of the present microorganisms and require an incubation time of more than two weeks (de Bruyn et al., 1990. *Applied and Environmental Microbiology* 56(9): 2891-2894) and this fact prevents their use to improve an ongoing bioleaching process. The fastest counting method based on microorganism culture is the floating filter technique, which decreases the incubation time to only 5 days (de Bruyn et al., 1990. *Applied and Environmental Microbiology* 56(9): 2891-2894). This methodology comprises filtrating microorganisms by using a polycarbonate membrane, which is placed in a liquid culture medium and kept in suspension by floating. The recovery of viable ferrooxidizing bacteria using this technique is approximately 57%.

Other alternatives have been developed with the object of reducing microbial viability analysis time, such as the determination of Fe(II) oxidizing activity (Escobar et al., 1996. Hydrometallurgy 40: 1-10) and the measurement of oxygen consumption rate (Savić et al., 2003. Proceedings of the 15th International Biohydrometallurgy Symposium, Athens, Greece, Sep. 14-19, 2003). However, these methods have the disadvantage of being indirect measurements and their execution requires large amounts of work and depends on the analyst's skill. A special case is the observation of individual cell viability under the microscope. As an example, Zanella et al. ("Biohydrometallurgical Technologies" (1993), Ed. A. E. Torma, M. L. Apel and C. L. Brierley, The Minerals, Metals and Materials Society, pp. 589-593) determined the physiological activity of *Acidithiobacillus ferrooxidans* cells by measuring the reduction of tetrazolium salts. Despite this method is effective to measure viability of *Acidithiobacillus ferrooxidans*, its practical application is limited by the difficulty of clearly distinguishing color changes of tetrazolium salts in real samples.

In the last years, the use of molecular biology techniques has become a very powerful tool to identify leaching microorganisms without microorganism culturing.

Accordingly, many different techniques have been developed at a research level to identify acidophilic microorganisms present in heap leaching effluents, in acid mine drainages, etc. (Pizarro et al., 1996. Appl. Environ. Microbiol. 62: 1323-1328., Espejo and Romero. 1997. Appl. Environ. Microbiol. 63:1344-1348. Vásquez and Espejo. 1997. Appl. Environ. Microbiol. 63:332-334, Schrenk et al., 1998. Science 279, Vásquez et al., 1999. Appl. Environ. Microbiol. 63:332-334, Bond et al., 2000. Appl. and Environ. Microbiol. 66: 3842-3849, Coram and Rawling, 2002. Applied and Environmental Microbiology 68(2):838-845, González-Toril et al., 2003, Mitchell et al., 2003. Proceedings of the 15th International Biohydrometallurgy Symposium, Athens, Greece, Sep. 14-19, 2003). Despite these techniques give valuable qualitative and quantitative information about the diversity of microbial communities that take part in leaching processes or are responsible for acid mine drainage formation, such techniques are not able to give an account of the activity or viability of such microorganisms.

An interesting potential alternative is the detection of bacterial ATP by using the enzymatic reaction between Luciferin and the enzyme Luciferase, which is used by fireflies to produce their characteristic light. The reaction has been proven to be proportional to the amount of microorganisms present in solution. This bioluminescence-based methodology has been used for determination of bacteria in wastewater effluents (Frosch et al. 1983, U.S. Pat. No. 4,385,113), in industrial waters, raw materials, intermediaries and products used in food, pharmaceutical, cosmetics, electronics and other industries, (Kawakami et al., 1994. U.S. Pat. No. 5,366,867; Seto, 1998. U.S. Pat. No. 5,766,868), in aqueous physiological fluids such as blood and urine (Picciolo and Chappelle, 1976, U.S. Pat. No. 3,971,703). Various technical solutions are known in the state of the art that allow this technique to be more efficient with regard to its methodology of analysis and to the equipments or apparatus to perform such technique (Aegidius, 1993, U.S. Pat. No. 5,258,285; Sanders, 1999, U.S. Pat. No. 5,888,725; Simpson and Hammond, 1991, U.S. Pat. No. 5,004,684; Foote et al., 1999, U.S. Pat. No. 5,962,247; DiCesare, 2003, U.S. Pat. No. 6,653,147; Schrecengost et al., 2003, U.S. Pat. No. 6,660,489 and McCaffrey, 2005, U.S. Pat. No. 6,927,851).

Despite the relevant development of the bioluminescence-based methodology, none of these documents describe a technique that could be applied to detect the presence of active acidophilic microorganisms that are important in bioleaching processes or responsible for the production of acid mine drainage. Measurement of active acidophilic microorganisms present in these samples has always had significant difficulties. The inconveniences that are present in the analysis of the growth of these microorganisms in laboratory culture media, the environment and bioleaching industrial processes, are the result of the diversity of inorganic compounds that are present in these environments (toxic metals, high salt concentration, etc.), the extreme conditions in which these microorganisms proliferate (particularly dominated by very low pH values) and the low cell density attained by these microorganisms in their growth. This has made their detection by means of bioluminescence techniques very difficult.

From the former exposition, it is evident the necessity of a method that allows a rapid, reliable and effective detection of the presence of active acidophilic microorganisms in water or solid samples, such as those present in bioleaching processes or in acid mine or rock drainages.

DETAILED DESCRIPTION OF THE INVENTION

Figure 1:
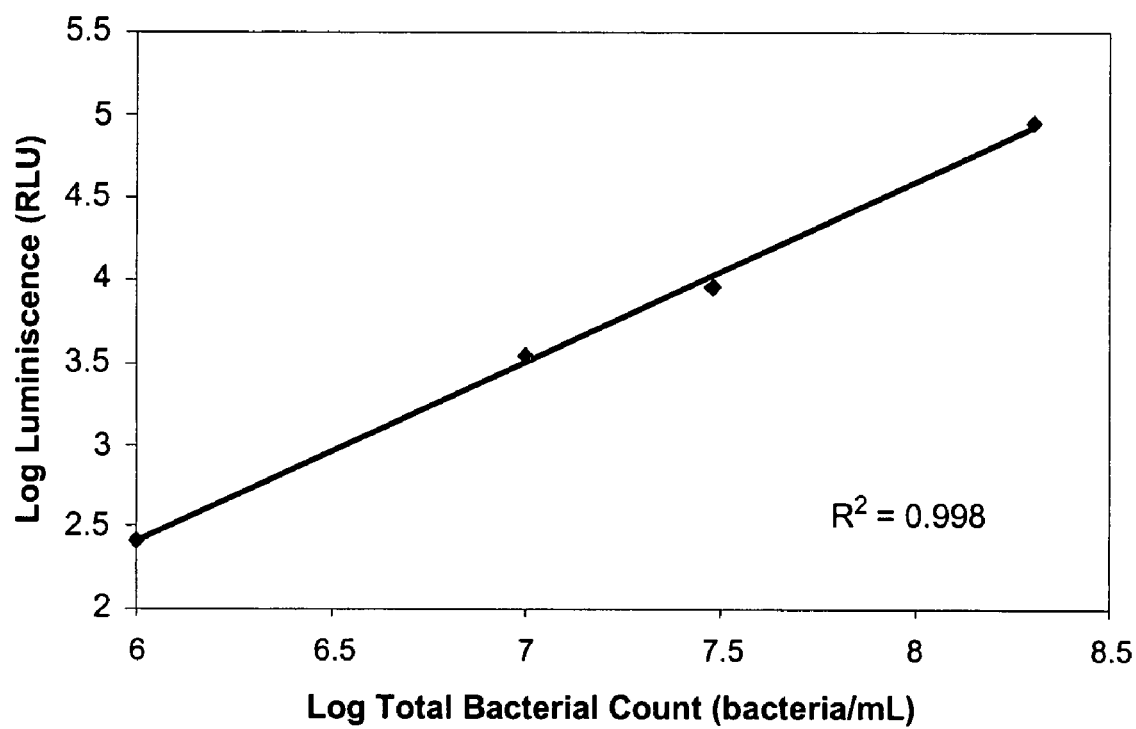
FIG. 1 shows a plot of the logarithm of luminescence results determined by the present invention, compared to a Petroff-Hausser counting chamber.

The present invention is characterized by the simplicity of the technique to attain a real measure of the viability of acidophilic cells present in a given acid solution sample, as for instance in bacterial leaching heaps or in acid mine drainage. In particular, according to this method, cells are subjected to a washing treatment that makes them able to enter into contact with luciferase without inactivating the enzyme. On the other hand, the application of bioluminescence to this type of samples has the advantage of not being interfered by the presence of other ATP sources such as animal or vegetal cell debris frequently associated with them, when compared to its common use in industrial effluents, food industry or clinical fluids.

The main object of the present invention is a rapid method for detection of the presence of active acidophilic microorganisms in aqueous samples, such as acid mine drainages or acid rock drainages, bioleaching solutions or solutions from heap leaching; or in solid samples, such as minerals or concentrates subjected to bioleaching or the like, such detection method comprising the following stages:

concentrating acidophilic microorganisms from a given volume of aqueous sample or from a suspension of microorganisms extracted from a solid sample;

removing the agents that are inhibitory for the bioluminescence reaction by washing the previously concentrated acidophilic microorganisms by means of one or more treatments with aqueous washing agents; and extracting adenosine-triphosphate (ATP) from the acidophilic microorganisms and measuring the light generated by such ATP by means of any bioluminescence detection system.

In one embodiment of the present invention, concentration of the acidophilic microorganisms is carried out by microfiltration. Particularly, microfiltration is carried out by using a microfiltration membrane, and polycarbonate or cellulose acetate membranes are preferentially used.

In another embodiment of the present invention, the microfiltration membranes used for concentration have a pore size that is adequate to retain microorganisms, preferably 0.22 μm or 0.45 μm. These microfiltration membranes are used with a filter holder.

In another embodiment of the present invention, concentration of the acidophilic microorganisms is carried out by filtration through hollow fibers.

In another embodiment of the present invention, concentration of the acidophilic microorganisms is carried out by centrifugation, preferably using a microcentrifuge.

In another embodiment of the present invention, concentration of acidophilic microorganisms is carried out by capturing acidophilic microorganisms by means of magnetic microparticles modified to bind microorganisms or by binding to any solid material modified to bind microorganisms. Particularly, such modification preferentially comprises antibody binding or coating with a hydrophobic compound.

In another additional embodiment of the present invention, the aqueous washing agent is a mineral acid solution. Particularly, said mineral acid is sulfuric acid. Preferably, the washing agent has a pH between 1 and 4.

In another additional embodiment of the present invention, the aqueous washing agent is distilled water, deionized water or a buffer having a pH close to neutrality.

In another particular embodiment of the present invention, the method for the detection of the presence of acidophilic microorganisms comprises a washing step of the acidophilic microorganisms that is carried out by sequentially treating them firstly with a mineral acid solution, which washes out salts that are present in solution without precipitating them, and secondly with distilled water, deionized water or a buffer having a pH close to neutrality, which allow removing the remaining bioluminescence inhibiting agents and reaching an adequate pH for the bioluminescence enzymatic reaction.

In another particular embodiment of the present invention, microorganisms are concentrated on the microfiltration membrane and are subsequently washed by one or more treatments with aqueous washing agents, which allow removing bioluminescence inhibiting agents.

According to an aspect of the present invention, the extraction of intracellular ATP is carried out by using an appropriate extracting agent, such as trichloroacetic acid (TCA), dimethyl sulfoxide (DMSO), perchloric acid, an organic solvent or a cationic surfactant. In a subsequent step, according to an embodiment of the present invention, ATP extracted from acidophilic microorganisms is contacted with a bioluminescence reactive that comprises luciferin or a derivative thereof and a luciferase, wherein said luciferin or the derivative thereof emit light in a bioluminescence reaction with luciferase in the presence of ATP. Particularly, the light emitted in a bioluminescence reaction can be measured by using a luminometer.

In another additional embodiment of the present invention, ATP extraction from acidophilic microorganisms can be carried out by using any commercially available bioluminescence detection system that contains all the reagents required for ATP extraction and the bioluminescence reaction. In particular, the detection system can be a bioluminescence-based device to determine surface hygiene.

In another particular embodiment of the invention, the method for detecting the presence of acidophilic microorganisms uses a cotton swab wetted with a rinsing solution to remove the acidophilic microorganisms retained on the microfiltration membrane surface by rubbing the swab on the membrane surface as many times as necessary; contacting the swab containing the acidophilic microorganisms with the device of said bioluminescence detection system that contains the extractant to release the intracellular ATP of such acidophilic microorganisms; contacting the solution containing the released ATP with the bioluminescence reagent; and introducing the device in a luminometer to determine the light emitted in a bioluminescence reaction.

For the analysis of a solid sample, such as minerals or concentrates, the present invention sets forth a specific embodiment, in which obtaining a suspension of microorganisms extracted from the solid sample is performed by using a previous extraction of acidophilic microorganism adhered to such solid sample with an aqueous solution is presented. Said previous extraction is carried out by treating the solid sample using a mechanical or chemical mechanism.

In other particular embodiment of this last aspect of the present invention, a mechanical treatment is used, which comprises suspending the solid sample in an aqueous solution and subjecting such sample to strong mechanical stirring or ultrasound; subsequently, separating the aqueous phase containing acidophilic microorganisms by decantation, filtration, centrifugation or other appropriate method known in the state of the art; and taking a given volume of the aqueous phase to carry out the detection of the presence of acidophilic microorganisms. Alternatively, a chemical treatment is used, which comprises suspending the solid sample in an aqueous solution containing tensioactive agents such as SDS, Tween 20 or Triton X-100; subsequently, separating the aqueous phase containing acidophilic microorganisms by decantation, filtration, centrifugation or other appropriate method known in the state of the art; and taking a given volume of the aqueous phase to carry out the detection of the presence of acidophilic microorganisms.

According to the invention, the method for detecting the presence of acidophilic microorganisms is applicable to the following acidophilic microorganisms: bacteria, archaea, fungi or microalgae.

In a particular embodiment of the present invention, bacteria preferably belong to genera *Acidithiobacillus, Leptospirillum, Sulfobacillus, Alicyclobacillus, Ferrimicrobium* or *Acidiphilium*.

In another particular embodiment of the present invention, archaea preferably belong to genera *Ferroplasma, Sulfolobus, Thermoplasma, Acidianus, Metallosphaera* or *Picrophilus*.

The second main object of the present invention is a kit for detection of the presence of active acidophilic microorganisms, which uses the previously described method and comprises at least one set of elements consisting of:
 one or more components useful to concentrate acidophilic microorganisms from a given volume of aqueous sample or from a suspension of microorganisms extracted from a solid sample;
 one or more washing solutions for the removal of bioluminescence reaction inhibiting agents; and
 a set of components and reagents for extraction of adenosine-triphosphate (ATP) from acidophilic microorganisms and for bioluminescence detection.

In a particular embodiment of the present invention, the kit components useful for concentration of acidophilic microorganisms are selected from the group consisting of: microfiltration membranes and filter holders for such microfiltration membranes, hollow-fiber cartridges, magnetic microparticles modified to bind microorganisms, solid materials modified to bind microorganisms or centrifuge tubes.

In another particular embodiment of the invention, the kit washing solutions for removal of bioluminescence reaction inhibiting agents include at least:
 one or more washing solutions comprising a mineral acid, preferably sulfuric acid; and/or
 one or more washing solutions having a pH close to neutrality, consisting of distilled water, deionized water or a buffer.

In another particular embodiment of the present invention, the set of kit components and reagents comprises at least a set of elements consisting of:
 an appropriate extracting agent, such as trichloroacetic acid (TCA), dimethyl sulfoxide (DMSO), perchloric acid, an organic solvent or a cationic surfactant.
 bioluminescence reagents comprising luciferin or a derivative thereof and a luciferase, wherein said luciferin or the derivative thereof emits light in a bioluminescence reaction with such luciferase in the presence of ATP; and
 a buffer comprising the salts required for the bioluminescence assay.

In another additional alternative embodiment of the present invention, the set of kit components and reagents for adenosine-triphosphate (ATP) extraction from acidophilic microorganisms and for bioluminescence detection is any commercially available bioluminescence detection system.

In one particular specific embodiment of the present invention, the detection system is a bioluminescence-based device to determine surface hygiene.

In another additional alternative embodiment of the present invention, the kit further comprises at least some of the following optional elements:
 a technical manual of use;
 one or more ATP-free pipettes;
 one or more automatic pipettes;
 one or more disposable Petri dish;
 one or more ATP-free pipette tips; and/or
 one or more ATP-free syringes.

Definitions

"Acidophilic microorganisms" comprise all microorganisms that are usually present in samples such as acid mine drainages or acid rock drainages, bioleaching solutions, heap leaching solutions, minerals or concentrates subjected to bioleaching or the like, said microorganisms growing usually at a pH lower or equal to 3. Among said microorganisms there are bacteria (e.g., bacteria belonging to genera *Acidithiobacillus, Leptospirillum, Sulfobacillus, Alicyclobacillus, Ferrimicrobium* or *Acidiphilium*), archaea (e.g., archaea belonging to genera *Ferroplasma, Sulfolobus, Thermoplasma, Acidianus, Metallosphaera* or *Picrophilus*), fungi and microalgae.

"Bioluminescence reaction inhibiting agents" are all chemical compounds such as metals, salts, acids and the like, that are usually present in samples such as acid mine drainages or acid rock drainages, bioleaching solutions, heap leaching solutions, minerals or concentrates subjected to bioleaching or the like, such chemical compounds causing a negative effect on light emission from ATP by means of the luciferin-luciferase reaction.

DESCRIPTION OF THE FIGURES

FIG. 1:

This figure shows a plot of the logarithm of luminescence results (RLU) determined by means of the method for detection of the presence of acidophilic microorganisms by bioluminescence, according to the present invention, compared to the logarithm of total bacterial count determined in a Petroff-Hausser counting chamber. A high correlation was found between these two types of assay ($R^2=0.9980$).

FIG. 2:

This figure shows a plot of the logarithm of luminescence results (RLU) determined by means of the method for detection of the presence of acidophilic microorganisms by bioluminescence, according to the present invention, compared to the logarithm of viable bacterial count (cfu/mL) determined by the floating filter method. A high correlation was found between these two types of assay ($R^2=0.9862$).

The following examples illustrate some concrete applications of the present invention, but are not meant to limit the framework or the scope of the present invention.

EXAMPLES

Example 1

Three 250 mL Erlenmeyer flasks containing 100 mL of the culture medium set forth in Table 1 were used in this example. To that end, the salts were dissolved one at a time in approximately 500 mL of distilled water and the solution volume is completed up to 1000 mL with distilled water. Solution pH was adjusted to 1.5 with sulfuric acid. The iron-containing culture media with all the components is autoclaved at 121° C. for 20 minutes, with previous accurate pH adjustment to avoid salt precipitation

TABLE 1

| Culture medium for *Acidithiobacillus ferrooxidans* | |
|---|---|
| Compound | Amount |
| $(NH_4)_2SO_4$ | 0.1 g/L |
| $MgSO_4 \cdot 7H_2O$ | 0.4 g/L |
| $K_2HPO_4 \cdot 3H_2O$ | 0.04 g/L |
| $FeSO_4 \cdot 7H_2O$ | 33.33 g/L |
| Distilled water | 950 ml |

Each flask was inoculated with 0.5 mL of a culture of *Acidithiobacillus ferrooxidans*, derived from strain ATCC 23270 (kindly provided by the Molecular Microbiology Laboratory, Faculty of Sciences, University of Chile). Subsequently, the flasks were incubated in an orbital shaker at 30° C. and 120 rpm.

After the culture was finished, total (viable and dead) bacterial counts were determined by microscopy. To that end, a culture sample was placed in a Petroff-Hausser counting chamber and at least 50 independent squares were counted. Counting was performed in a direct sample or in a dilution thereof, depending on the amount observed in a first sample. Average is calculated and the result is multiplied by a conversion factor to obtain the total bacterial count as bacteria/mL. Microscopic observations were made by using a Carl Zeiss microscope (Germany) equipped with phase contrast and using a 400× magnification.

In parallel, the rapid method for detection of the presence of acidophilic microorganisms by bioluminescence was performed. As a first stage, acidophilic microorganisms were concentrated from a given volume of the aqueous sample. To that end, 10 mL of the microorganism culture to be assayed were passed through a filter holder with a white 0.22 μm polycarbonate membrane by means of a syringe or by using a vacuum pump. The filtered culture media was collected in a sterile tube and conserved as culture control.

In a second stage of this assay, removal of the agents that are inhibitory for the bioluminescence reaction was carried out by sequentially washing the previously concentrated acidophilic microorganisms. To that end, 20 mL of water acidified with sulfuric acid (pH 1.8) were passed through the filter. The filtrate was discarded. Then the membrane was rinsed with 20 mL of distilled water and the filtrate was discarded again. Finally, air is allowed to pass through the membrane to remove any water remnant (by using moderate pressure over a syringe plunger or a vacuum pump).

In a third stage of the assay, extraction of intracellular adenosine-triphosphate (ATP) from the acidophilic microorganisms and measurement of the light generated by such ATP by means of any bioluminescence detection system are carried out. To that end, the polycarbonate membrane that supports the concentrated acidophilic bacteria on its surface is carefully removed from the filter holder with tweezers, and the membrane is placed on a sterile Petri dish. At this moment, the sample is ready to be assayed by using the luciferin/luciferase enzymatic reaction for detection of acidophilic microorganisms. For this example, the bioluminescence Hy-Lite® kit (Merck, Germany) for surface hygiene assessment was used. The swab was wetted by immersion in a rinsing solution, and is rubbed against the surface of the membrane, keeping a constant pressure and without touching the surface of the Petri dish. The reaction device included with this kit was used to extract ATP and carry out the bioluminescence reaction according to the manufacturer's protocol. Finally, emitted light was immediately measured in a luminometer. The values obtained are expressed in relative light units (RLU). All the detection analysis for *Acidithiobacillus ferrooxidans* from an aqueous sample is carried out in a matter of minutes. The assay duration can vary from 15 and 30 minutes, depending on the user.

TABLE 2

Comparison of method of microscopic total bacterial counting in a Petroff-Hausser chamber and the bioluminescence method for the detection of *Acidithiobacillus ferrooxidans* at different culture times.

| Culture time (days) | Total count method (Bacteria/mL) | Bioluminescence method (RLU)[1] |
| --- | --- | --- |
| 3 | $3.4 \times 10^7$ | 21,817 |
| 5 | $1.8 \times 10^8$ | 21,000 |
| 12 | $1.2 \times 10^8$ | 26,517 |
| 22 | $3.2 \times 10^8$ | 2,703 |
| 48 | $2.9 \times 10^8$ | 963 |
| 70 | $6.7 \times 10^7$ | 849 |

[1]Triplicate average measurement

Table 2 shows a comparison of the results obtained with the method of microscopic total bacteria counting in a Petroff-Hausser chamber and the bioluminescence method for the detection of *Acidithiobacillus ferrooxidans*. At different culture times, the microscopic total bacterial count remain substantially constant. However, the same culture analyzed by using the bioluminescence method shows high light emission values (RLU) between days 3 and 12, when the cultures are more metabolically active and have high intracellular ATP concentrations. In changes starting from day 22 on, the light emission values (RLU) start to descend markedly, due to culture aging.

This example shows that thanks to the acidophilic microorganism concentration and inhibiting agent removal stages according to the present invention, it is possible to attain high light emission values from ATP from the acidophilic bacterium *Acidithiobacillus ferrooxidans* despite the existence of different agents or chemical compounds in the culture medium that are inhibitory for the bioluminescence reaction, such as an extremely low pH and high metal concentration such as high iron concentration. On the other hand, it is evident the ability of the bioluminescence method to discriminate between metabolically active and inactive bacteria, which represents an advantage over the methods that measure only total bacteria. Regarding the methods that determine viability by culture, the present invention is advantageous because it reduces the analysis time from 7 to 14 days to only a few minutes.

Comparative Example 1

The following comparative example is included to show the difficulties that appear when trying to perform the bioluminescence analysis for acidophilic microorganisms if the sample preparation method provided in this invention is not used. To that end, *Acidithiobacillus ferrooxidans* was cultured during 13 days and bioluminescence was determined in the same way set forth in Example 1, by carrying out sample concentration by means of microfiltration membranes and inhibiting agents' removal by means of sequential washings with an acid solution and distilled water. As a comparison, in a second case the same protocol was carried out by performing a culture concentration using a microfiltration membrane but without the washing steps. Finally, a direct determination is carried out on the sample (without concentration and without washing steps).

TABLE 3

Comparison of the bioluminescence measurement for *Acidithiobacillus ferrooxidans* detection by using different sample treatments.

| Treatment | Bioluminescence measurement (RLU) |
| --- | --- |
| As in Example 1 | 34,442 |
| As in Example 1, but without washings for the removal of inhibiting compounds | 1,400 |

In Table 3, it is possible to observe a very low bioluminescence measurement level (only 4%) when no washing steps are used for the removal of inhibiting compounds in comparison with the result obtained by the method of Example 1. When a direct determination is made on the sample (without concentration and washings) no results are obtained, due to low bacterial concentration, low pH and presence of enzyme inhibiting compounds.

Example 2

Three 250 mL Erlenmeyer flasks containing 100 mL of the culture medium set forth in Table 4 were used in this example. To that end, solution A is prepared by dissolving the salts one by one in 990 mL of distilled water. Solution pH was adjusted to 4.4-4.7 by using sulfuric acid and the solution was sterilized in an autoclave at 121° C. for 20 minutes. In parallel, solution B was prepared by dissolving sodium thiosulfate pentahydrate in 10 mL of distilled water and was sterilized by filtration using cellulose acetate membranes having a pore size of 0.22 µm. After sterilization, solutions A and B were mixed in such a way that 1 mL of filtered solution B was added to 100 mL of solution A.

TABLE 4

Medium 71 for *Acidithiobacillus thiooxidans*

| Compound | Amount |
| --- | --- |
| Solution A | |
| $KH_2PO_4$ | 3 g |
| $MgSO_4 7H_2O$ | 0.5 g |
| $(NH_4)_2SO_4$ | 3 g |
| $CaCl_2 \cdot H_2O$ | 0.25 g |
| Solution B | |
| $Na_2S_2O_3 \cdot 5H_2O$ | 5 g |

Each flask was inoculated with 0.5 mL of a culture of *Acidithiobacillus thiooxidans* strain DSMZ 14887. Subsequently, the flasks were incubated in an orbital shaker at 30° C. and 120 rpm.

After the culture was finished total bacterial counts were determined and the rapid method for detection of the presence of acidophilic microorganisms by bioluminescence according to the description of Example 1.

Table 5 shows a comparison of the results obtained with the method of microscopic total bacteria counting in a Petroff-Hausser chamber and the bioluminescence method for the detection of *Acidithiobacillus thiooxidans*. The result obtained show the same tendency observed in Example 1 for *Acidithiobacillus ferrooxidans*, wherein at different culture days total bacterial counts remain substantially constant in time, whereas the high initial light emission (RLU) measurement decreases with culture age.

TABLE 5

Comparison of method of microscopic total bacteria counting in a Petroff-Hausser chamber and the bioluminescence method for the detection of *Acidithiobacillus thiooxidans*.

| Culture time (days) | Total count method (Bacteria/mL) | Bioluminescence method (RLU)[1] |
|---|---|---|
| 5 | $3.33 \times 10^8$ | 114,833 |
| 12 | $1.85 \times 10^8$ | 53,377 |
| 20 | $2.73 \times 10^8$ | 36,637 |
| 27 | $2.00 \times 10^8$ | 470 |

[1]Triplicate average measurement

In this example, it is possible to assess that the bioluminescence method is able to discriminate between metabolically active and inactive bacteria, and it is possible to further confirm the advantages of the bioluminescence method when compared to the traditional viable acidophilic microorganism counting techniques, due to the easiness of the analytic technique.

Example 3

Three 250 mL Erlenmeyer flasks containing 100 mL of the culture medium set forth in Table 6 were used in this example. To that end, solution A is prepared by dissolving the salts one by one in 950 mL of distilled water. Solution pH was adjusted to 1.8 by using sulfuric acid and the solution was sterilized in an autoclave at 121° C. for 20 minutes. In parallel, solution B is prepared by dissolving ferrous sulfate heptahydrate in 50 mL of 0.25 N sulfuric acid. Solution pH was adjusted to 1.2. The solution was sterilized in an autoclave at 121° C. for 20 minutes. Additionally, solution C is prepared by dissolving the salts one by one in 1 L of distilled water. Solution pH was adjusted to 1.8 by using sulfuric acid and the solution was sterilized in an autoclave at 121° C. for 20 minutes. After sterilization, solutions A and B are mixed and 1 mL of solution C is added.

Each flask is inoculated with 0.5 mL of a culture of *Leptospirillum ferrooxidans* strain DSMZ 2705. Subsequently, the flasks were incubated in an orbital shaker at 30° C. and 120 rpm.

TABLE 6

Culture medium 882 for *Leptospirillum ferrooxidans*

| Compound | Amount |
|---|---|
| Solution A | |
| $(NH_4)_2SO_4$ | 132 mg |
| $MgCl_2 \cdot 6H_2O$ | 53 mg |
| $KH_2PO_4$ | 27 mg |
| $CaCl_2 \cdot H_2O$ | 147 mg |
| Distilled water | 950 mL |
| Solution B | |
| $FeSO_4 \cdot 7H_2O$ | 20 g |
| $H_2SO_4$, 0.25N | 50 mL |
| Solution C: trace elements | |
| $MnCl_2 \cdot 2H_2O$ | 62 mg |
| $ZnCl_2$ | 68 mg |
| $CoCl_2 \cdot 6H_2O$ | 64 mg |
| $H_3BO_3$ | 31 mg |
| $Na_2MoO_4$ | 10 mg |

TABLE 6-continued

Culture medium 882 for *Leptospirillum ferrooxidans*

| Compound | Amount |
|---|---|
| $CuCl_2 \cdot H_2O$ | 67 mg |
| Distilled water | 1000 mL |

After the culture was finished total bacterial counts were determined and the rapid method for detection of the presence of acidophilic microorganisms by bioluminescence according to the description of Example 1.

Table 7 shows a comparison of the results obtained with the method of microscopic total bacterial counting in a Petroff-Hausser chamber and the bioluminescence method for the detection of *Leptospirillum ferrooxidans*. The result obtained show the same tendency observed in Example 1, and total bacterial count remain substantially constant in time at different culture days, whereas the high initial light emission (RLU) measurement decreases with culture age.

TABLE 7

Comparison of method of microscopic total bacterial counting in a Petroff-Hausser chamber and the bioluminescence method for the detection of *Leptospirillum thiooxidans*.

| Culture time (days) | Total count method (Bacteria/mL) | Bioluminescence method (RLU)[1] |
|---|---|---|
| 7 | $5.85 \times 10^8$ | 17,324 |
| 13 | $1.93 \times 10^8$ | 1,163 |

[1]Triplicate average measurement

In this example, it is possible to assess that the bioluminescence method is able to discriminate between metabolically active and inactive bacteria, and it is possible to further confirm the advantages of the bioluminescence method when compared to the traditional viable acidophilic microorganism counting techniques, due to the easiness of the analytic technique.

Example 4

In this example, a correlation between the method for detection of the presence of acidophilic microorganisms by bioluminescence and other methods currently used to determine the count of these microorganisms is determined. To that end, *Acidithiobacillus ferrooxidans* is cultured in Erlenmeyer flasks for 4 days according to Example 1. Subsequently, determinations of different samples by the bioluminescence method, microscopic total bacterial count determination in a Petroff-Haussser counting chamber and total viable bacterial count by the floating filter method described by de Bruyn et al. (1990, *Applied and Environmental Microbiology* 56(9): 2891-2894) were made in parallel by using different dilutions of an *Acidithiobacillus ferrooxidans* culture.

FIG. 1 shows a high correlation between the method for detection of the presence of acidophilic microorganisms by bioluminescence and the total bacterial count in a Petroff-Hausser counting chamber ($R^2=0.9980$). It is important to note (taking into account the results of Example 1, Table 2) that this is possible because a young very active culture (4 days old) was used.

Figure 2:
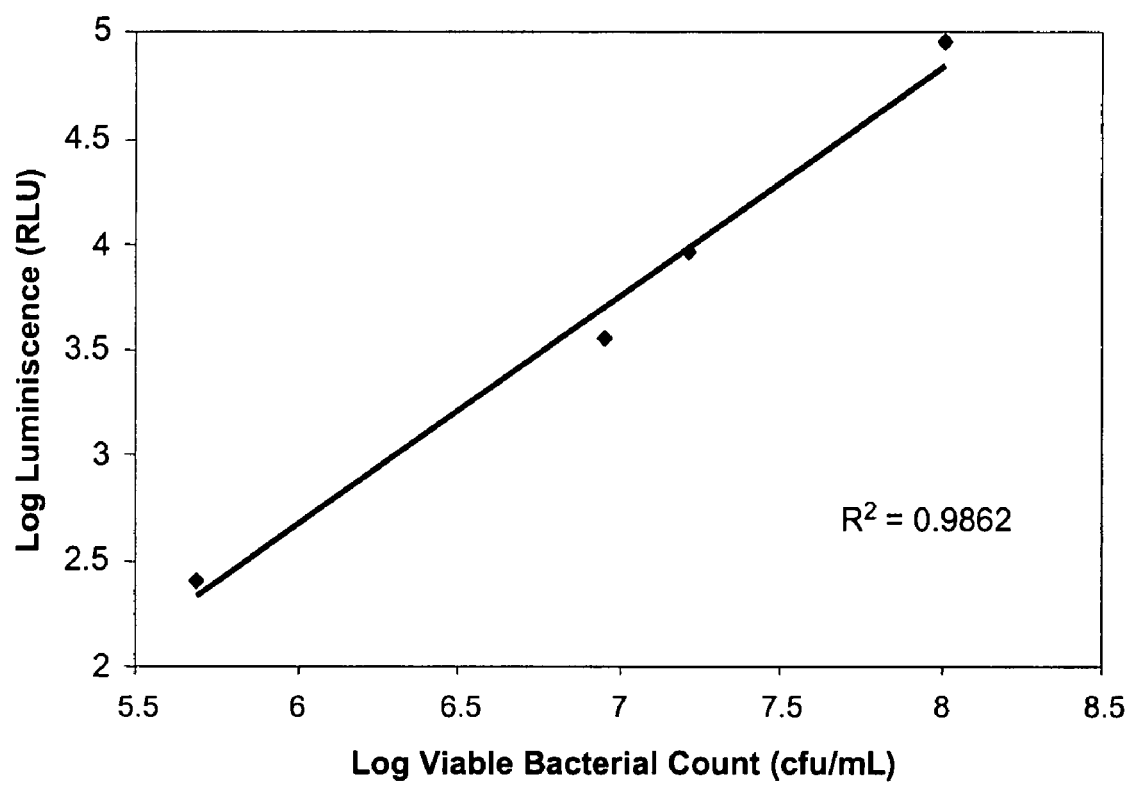
FIG. 2 shows a plot of the logarithm of luminescence results determined by the present invention, compared the logarithm of variable bacteria count determined by the floating filter method.

FIG. 2 shows a high correlation between the method for detection of the presence of acidophilic microorganisms by bioluminescence and the viable bacterial count determined by using the floating filter method ($R^2=0.9862$). This last result is very important because detection of metabolically active microorganisms is a relevant parameter for the operation and control of industrial scale bioleaching processes.

What is claimed is:

1. A method of analysis of the presence of active acidophilic microorganisms in a bioleaching solution, comprising the steps of:
concentrating the bioleaching solution, resulting in a concentrated solution;
removing luminescence inhibitory agents from the concentrated solution;
wherein the step of removing luminescence inhibitory agents includes:
first, treating the concentrated solution with a mineral acid solution to obtain a treated solution; and
second, treating the treated solution with an agent selected from the group consisting of: distilled water, deionized water and a buffer with a pH close to neutrality to obtain an inhibitory agent free solution;
initiating a bioluminescence reaction with said inhibitory agent free solution;
measuring the light emitted in the bioluminescence reaction involving active acidophilic microorganisms in a concentrated solution; and
correlating the measured light emitted to determine the presence of active acidophilic microorganisms in the bioleaching solution.

2. The method of claim 1, wherein the step of concentrating the solution includes microfiltration.

3. The method of claim 2, wherein the microfiltration employs a microfiltration membrane.

4. The method of claim 3, wherein the microfiltration membrane is one of a polycarbonate membrane and a cellulose acetate membrane.

5. The method of claim 1, wherein the step of concentrating includes filtration through hollow fibers.

6. The method of claim 1, wherein the step of concentrating includes centrifuging.

7. The method of claim 6, wherein the centrifuge is a microcentrifuge.

8. The method of claim 1, wherein the step of concentrating includes binding the acidophilic microorganisms using magnetic microparticles.

9. The method of claim 1, wherein the step of concentrating includes binding the acidophilic microorganisms to a solid material.

10. The method of claim 8, wherein the magnetic microparticles are prepared by linking an antibody to the magnetic microparticle.

11. The method of claim 9, wherein the solid material is prepared by a hydrophobic compound coating process.

12. The method of claim 1, wherein the step of initiating said bioluminescence reaction includes using an extracting agent selected from the group consisting of: trichloroacetic acid, dimethyl sulfoxide, perchloric acid, an organic solvent and a cationic surfactant.

13. The method of claim 1, wherein the step of initiating said bioluminescence reaction includes applying, to the inhibitory agent free solution, a bioluminescence reactive agent selected from the group consisting of: luciferin and a luciferin derivative.

14. The method of claim 1, wherein the step of measuring includes using a luminometer.

15. The method of claim 3, wherein the step of initiating said bioluminescence reaction further comprises:
collecting said acidophilic microorganisms from said inhibitory agent free solution with a microfiltration membrane;
wetting a cotton swab with a rinsing solution;
removing acidophilic microorganisms from the microfiltration membrane using the cotton swab; and
contacting the cotton swab with a solution selected from the group consisting of: luciferin and a luciferin derivative.

16. The method of claim 1, wherein the acidophilic microorganisms are selected from the group consisting of: bacteria, archaea, fungi and microalgae.

17. The method of claim 1, wherein the acidophilic microorganisms are bacteria belonging to a genus selected from the group consisting of: *Acidithiobacillus, Leptospirillum, Sulfobacillus, Alicyclobacillus, Ferrimicrobium* and *Acidiphilium*.

18. The method of claim 1, wherein the acidophilic microorganisms are archaea belonging to a genus selected from the group consisting of: *Ferroplasma, Sulfolobus, Thermoplasma, Acidianus, Metallosphaera* and *Picrophilus*.

19. A method of analysis of the presence of active acidophilic microorganisms in a bioleaching solution, comprising the steps of:
concentrating the bioleaching solution, resulting in a concentration of acidophilic microorganisms;
removing luminescence inhibitory agents from the concentration of acidophilic microorganisms;
wherein the step of removing luminescence inhibitory agents includes:
first, treating the concentration of acidophilic microorganisms with a mineral acid solution to obtain a treated solution; and
second, treating the treated solution with an agent selected from the group consisting of: distilled water, deionized water and a buffer with a pH close to neutrality to obtain an inhibitory agent free solution;
initiating a bioluminescence reaction with said inhibitory agent free solution;
measuring the level of adenosine-triphosphate extracted from said inhibitory agent free solution during the bioluminescence reaction; and
correlating the level of adenosine-triphosphate extracted to determine the presence of active acidophilic microorganisms in the bioleaching solution.

* * * * *

UNITED STATES PATENT AND TRADEMARK OFFICE
CERTIFICATE OF CORRECTION

PATENT NO.       : 7,851,177 B2
APPLICATION NO.  : 11/880565
DATED            : December 14, 2010
INVENTOR(S)      : Pabla Viedma It is certified that error appears in the above-identified patent and that said Letters Patent is hereby corrected as shown below:

On the cover page at section (73):

Delete "Biotechnologias" and insert -- Biotecnologias --

Signed and Sealed this
Twenty-second Day of February, 2011

David J. Kappos
*Director of the United States Patent and Trademark Office*